(12) United States Patent
Zhao

(10) Patent No.: US 11,283,161 B2
(45) Date of Patent: Mar. 22, 2022

(54) ANTENNA FOR IMPLANTABLE MEDICAL DEVICES

(71) Applicant: Medtronic, Inc., Minneapolis, MN (US)

(72) Inventor: Yanzhu Zhao, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/515,449

(22) Filed: Jul. 18, 2019

(65) Prior Publication Data
US 2021/0021020 A1    Jan. 21, 2021

(51) Int. Cl.
*H01Q 1/27* (2006.01)
*H01Q 9/04* (2006.01)

(52) U.S. Cl.
CPC ........... *H01Q 1/273* (2013.01); *H01Q 9/0414* (2013.01); *H01Q 9/0442* (2013.01)

(58) Field of Classification Search
CPC combination set(s) only.
See application file for complete search history.

(56) References Cited

U.S. PATENT DOCUMENTS

| | | | |
|---|---|---|---|
| 6,230,059 B1 | 5/2001 | Duffin | |
| 6,412,490 B1 | 7/2002 | Lee | |
| 9,622,778 B2 | 4/2017 | Wengreen et al. | |
| 2007/0260294 A1* | 11/2007 | Schulman | A61N 1/375 607/60 |
| 2007/0288066 A1 | 12/2007 | Christman | |
| 2009/0270948 A1 | 10/2009 | Nghiem et al. | |
| 2010/0019985 A1* | 1/2010 | Bashyam | A61N 1/37229 343/873 |
| 2011/0001610 A1 | 1/2011 | Stevenson et al. | |
| 2012/0283705 A1 | 11/2012 | Lee et al. | |
| 2014/0133123 A1* | 5/2014 | Prasannakumar | A61N 1/37229 361/814 |
| 2017/0065207 A1 | 3/2017 | Landherr et al. | |
| 2017/0281957 A1 | 10/2017 | Howard | |

OTHER PUBLICATIONS

International Search Report dated Sep. 29, 2020, corresponding to counterpart Application No. PCT/US2020/04060; 3 pages.
Written Opinion of the International Searching Authority dated Sep. 29, 2020, corresponding to counterpart Application No. PCT/US2020/04060; 5 pages.

* cited by examiner

*Primary Examiner* — Jimmy T Vu
(74) *Attorney, Agent, or Firm* — Shumaker & Sieffert, P.A.

(57) ABSTRACT

The disclosure describes examples of antennas used for communication with an implantable medical device (IMD). As one example, the IMD includes a housing configured to house communication circuitry within an internal side of the housing, and a planar antenna, having a curved structure, that is stacked on an external side of the housing and coupled to the communication circuitry. As another example, the IMD includes a housing configured to house communication circuitry within an internal side of the housing and an antenna having a curved structure formed on an external side of the housing and coupled to the communication circuitry. A resonant frequency of the antenna is based on a dielectric constant of tissue surrounding the antenna when the IMD is implanted, and a current distribution of the antenna is in-phase in opposite sides of the antenna.

24 Claims, 8 Drawing Sheets

ANTENNA FOR IMPLANTABLE MEDICAL DEVICES

TECHNICAL FIELD

The disclosure relates to medical device communication and, more particularly, to an antenna for an implantable medical device.

BACKGROUND

Various implantable medical devices have been clinically implanted or proposed for therapeutically treating or monitoring one or more physiological and/or neurological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, implantable loop recorders, and pressure sensors, among others. Such devices may be associated with leads that position electrodes or sensors at a desired location, or may be leadless with electrodes or sensors integrated into the device housing. These devices may have the ability to wirelessly transmit data either to another device implanted in the patient or to another device located externally of the patient, or both.

Although implantation of some devices requires a surgical procedure, other devices may be small enough to be delivered and placed at an intended implant location in a minimally invasive manner, such as by a percutaneous delivery catheter or transvenously. By way of illustrative example, implantable miniature sensors have been proposed and used in blood vessels to measure directly the diastolic, systolic and mean blood pressures, as well as body temperature and cardiac output of a patient. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. In addition, miniaturized pacemakers that may be implanted directly within a patient's heart, with or without the need for leads to position electrodes, have been proposed, built, and adapted to provide pacing and other electrical therapy to the patient.

These example devices communicate with external devices or other devices implanted within the patient. For example, the devices transmit information indicative of the sensed data. The devices receive information such as therapy and sensing parameters and other information that defines modes of operation.

SUMMARY

The disclosure describes medical devices, systems, and associated techniques, structures, and assemblies including or involving an antenna that may be used to provide communications between medical devices and one or more other device(s). In some examples, the medical devices that include these antennas may be small devices and may have been implanted within the patient under the skin or even relatively deeper within the patient, for example implanted on or within the heart of a patient.

As described in more detail, this disclosure describes examples of an antenna having a curved (e.g., closed or partly open) structure with feed points that cause for an in-phase current distribution at a resonant frequency. Due to the in-phase current distribution, the antenna described in this disclosure may not be sensitive to tissue conductivity. Accordingly, the antenna can be formed external to the implantable medical device such as a planar antenna that is stacked on the housing. In some examples, when implanted, the antenna may be in direct contact with patient tissue or very thin insulation may separate the antenna from the patient tissue.

In one example, the disclosure describes an implantable medical device (IMD) comprising a housing configured to house communication circuitry within an internal side of the housing, and a planar antenna, having a curved structure, that is stacked on an external side of the housing and coupled to the communication circuitry.

In one example, the disclosure describes a method of manufacturing an implantable medical device (IMD), the method comprising forming a housing configured to house communication circuitry within an internal side of the housing, stacking a planar antenna, having a curved structure, on an external side of the housing, and coupling the planar antenna with the communication circuitry.

In one example, the disclosure describes an implantable medical device (IMD) comprising a housing configured to house communication circuitry within an internal side of the housing, and an antenna having a curved structure formed on an external side of the housing and coupled to the communication circuitry. A resonant frequency of the antenna is based on a dielectric constant of tissue surrounding the antenna when the IMD is implanted, and a current distribution of the antenna is in-phase in opposite sides of the antenna.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
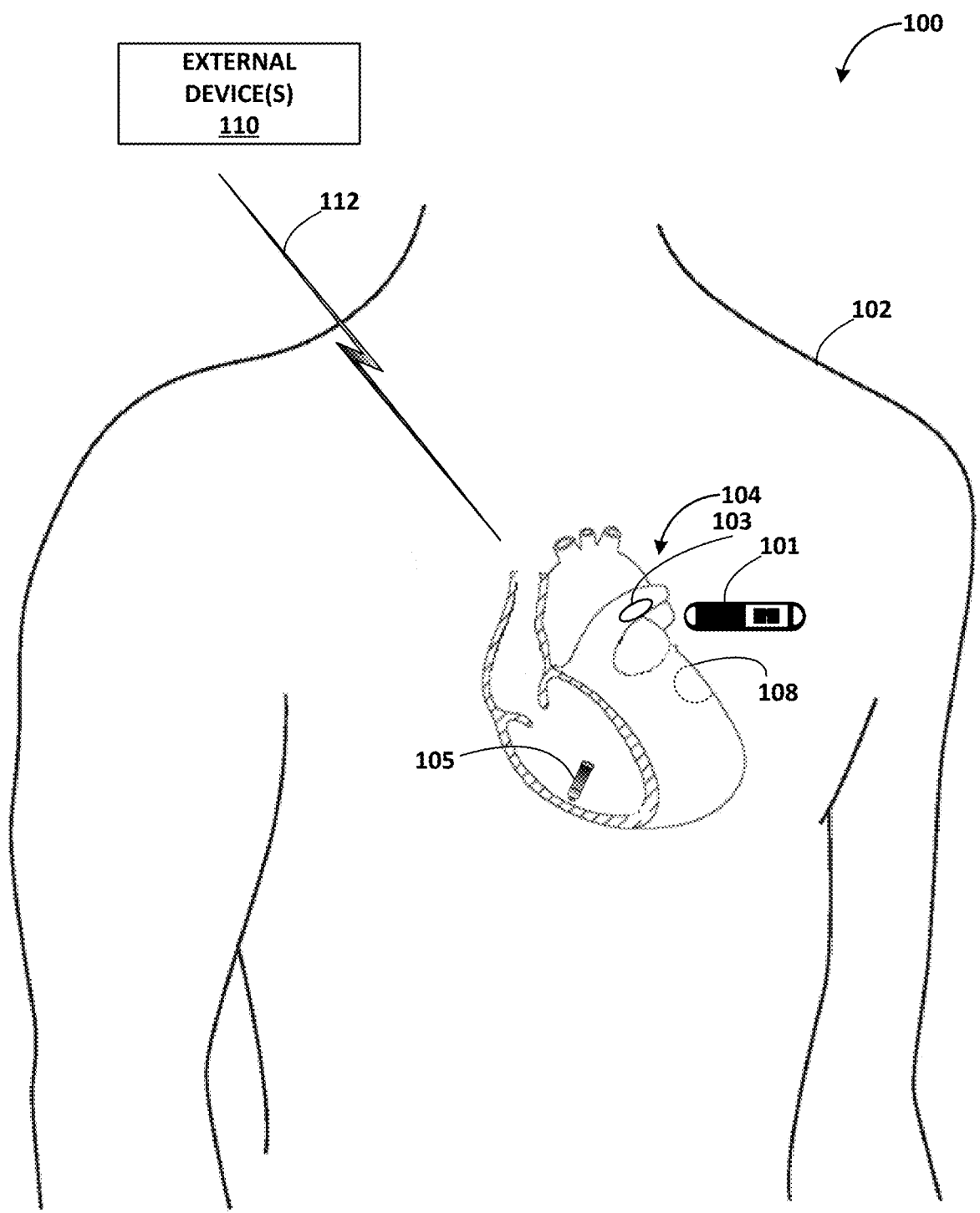
FIG. 1 is a conceptual drawing illustrating an example medical device system in conjunction with a patient according to various examples described in this disclosure.

This disclosure generally relates to examples of antennas that are formed on a housing of a medical device. The example antennas may take form of a curved (e.g., closed or partly open) structure (e.g., rectangle, circular, elliptical, etc.) with feed points for a current to flow through the example antennas. As described in more detail, the combination of the feed points and the curved structure cause the current to distribute in-phase in the example antennas. For instance, the direction of the current on one side of the curved structure is the same as the direction of the current on the opposite side of the curved structure.

Moreover, the example antennas may not be as sensitive to conductivity of patient tissue because the antenna provides a lower impedance path of the current as compared to impedance through tissue. For instance, due to the in-phase distribution of the current in the example antennas, the current is more likely to flow through the antenna than through tissue. Because the example antennas may not be sensitive to the conductivity of patient tissue, it may be possible to form the example antennas on the housing of the medical device such that when the medical device is implanted, an antenna of the medical device is in contact with the patient tissue.

Patient tissue tends to have a relatively high dielectric constant, especially as compared to air or polymers used to insulate existing antennas. For a given resonant frequency, a size of an antenna is inversely proportional to the dielectric constant (e.g., for a low dielectric constant, the size of the antenna needs to be bigger for the same resonant frequency as an antenna surrounded by a higher dielectric constant). Because the example antennas described in this disclosure can be in contact with the patient tissue, the example antennas described in this disclosure may be in an environment with relatively high dielectric constant and can therefore have a relatively small size. The example antennas may be planar antennas (e.g., virtually no volume) and formed on the housing of the medical device such that when the medical device is implanted, the antenna is in contact with the patient tissue.

For instance, some other antennas that cannot be in contact with tissue (e.g., due to sensitivity to the conductivity of tissue) are formed within a header and surrounded by a polymer with relatively low dielectric constant. This header is then connected to the medical device. Due to the relatively low dielectric constant, the size of these other antennas become too large to be formed on a side of the housing with very little volume.

Accordingly, this disclosure describes examples of antennas that can be formed on an external side of the medical device such that the antennas utilize minimum volume. This results in an overall smaller medical device, as compared to other medical devices having a header that houses the antenna, which is beneficial for implantation.

As described above, one of the reasons that the example antennas described in this disclosure may be smaller than antennas in a header is because the example antennas are in contact with patient tissue when implanted. In this disclosure, "in contact" may refer to the antennas being surrounded by material having a dielectric constant set by the patient tissue such that the resonant frequency of the antennas is a function of a dielectric constant of the patient tissue. Stated another way, the functionality and operational characteristics of the antennas is based on a dielectric constant of the patient tissue. For instance, in some examples, the antennas may be in direct contact with the patient tissue. However, it may be possible that in some examples, a protective coating is applied to the antenna to protect the antenna from damage. Even in such a scenario, the antenna may be considered as being "in contact" with patient tissue because the dielectric constant of the tissue is determinative of the resonant frequency of the antenna.

FIG. 1 is a conceptual drawing illustrating an example of some components of a medical device system 100 in conjunction with a patient 102 according to various examples described in this disclosure. The systems, devices, and techniques described in this disclosure provide implantable medical devices (IMDs) that may include an antenna arranged in a manner further described throughout this disclosure, to communicatively link the IMD(s) with one or more external device(s) 110, and/or to each other, as further described below. System 100 may include a single IMD, such as IMD 101, implanted in patient 102. As one example, IMD 101 may be inserted just under skin in an out-patient procedure. IMD 101 may be an insertable cardiac monitor (ICM), as one example.

Also, for ease of illustration, system 100 includes a plurality of IMDs. However, the techniques described in this disclosure do not require the use of a plurality of IMDs. In some examples, system 100 may include only one IMD (e.g., IMD 101). Also, the example techniques are not necessarily limited to implantable medical devices, and may be extended to other devices such as wearable medical devices such as where the antenna may still be in contact with the skin of the patient (e.g., glucose sensor/pump), non-medical wearable devices (e.g., monitoring devices worn on externally that monitor steps, pulse rate, etc.), and other devices including cell phone.

System 100 in some examples includes a plurality of IMDs, for example some combination of IMD 101, IMD 103, and/or IMD 105, as further described below. In various examples, at least one of the IMDs in system 100 includes an antenna configured as described in this disclosure. Also, in some examples, there may only be on IMD (e.g., IMD 101) For purposes of this disclosure, knowledge of cardiovascular anatomy is presumed, and details are omitted except to the extent necessary or desirable to explain the context of the techniques of this disclosure. Although the example techniques are described with respect to the heart, the example techniques are not limited to cardiac therapy. For instance, the example techniques described in this disclosure may be extended to non-cardiac medical devices that provide communication (e.g., devices for pain stimulation, brain stimulation, pelvic stimulation, spinal stimulation, etc. and devices such as implanted drug pumps, and the like).

As illustrated in FIG. 1, system 100 includes IMD 101 which may be an insertable cardiac monitor (ICM) capable of sensing and recording cardiac electrogram (EGM) (also referred to as an electrocardiogram, ECG, or EKG when external electrodes are placed on the skin) signals from a position outside of heart 104 via electrodes (not shown in FIG. 1). In some examples, IMD 101 includes or is coupled to one or more additional sensors, such as accelerometers, that generate one or more signals that vary based on patient motion and/or posture, blood flow, or respiration. Examples of IMD 101 may monitor a physiological parameter indicative of patient state, such as posture, heart rate, activity level, and/or respiration rate. IMD 101 may be implanted outside of the thorax of patient 102, e.g., subcutaneously or submuscularly, such as the pectoral location illustrated in FIG. 1. In some examples, IMD 101 may take the form of a Reveal LINQ® ICM, available from Medtronic plc, of Dublin, Ireland. In other examples, IMD 101 may be a pacemaker, e.g., configured to sense electrical activity of heart 104, and/or to deliver pacing therapy, e.g., bradycardia pacing therapy, cardiac resynchronization therapy (CRT), anti-tachycardia pacing (ATP) therapy, and/or post-shock pacing, to heart 104, e.g., via intracardiac or extracardiac leads (not shown), and/or a cardioverter/defibrillator configured to detect tachyarrhythmias and deliver anti-tachyarrhythmia shocks to heart 104 via the one or more leads.

In various examples, IMD 101 is configured to wirelessly communicate with one or more external device(s) 110 as illustratively shown in FIG. 1 by communication link 112. External device(s) 110 may be a computing device, e.g., used in a home, ambulatory, clinic, or hospital setting, to wirelessly communicate with IMD 101. For example, external device(s) 110 may be a patient monitor, such as the MyCareLink™ patient monitor, or a programming instrument, such as the CareLink SmartSync™ system, available from Medtronic Inc., a subsidiary of Medtronic plc of Dublin, Ireland. In another example, external device(s) 110 may be a mobile computing device such as a smartphone, tablet, smartwatch, or other wearable or portable device. External device(s) 110 may, for example, include a mobile application, such as MyCareLink Heart™ mobile app, available from Medtronic Inc., a subsidiary of Medtronic plc of Dublin, Ireland, that enables external device(s) 110 to communicate with IMD 101. External device(s) 110 may be coupled to a remote patient monitoring system, such as CareLink™ Network, available from Medtronic Inc., a subsidiary of Medtronic plc, of Dublin, Ireland. External device(s) 110 may be, as examples, a programmer, external monitor, or consumer device, e.g., smart phone. External device(s) 110 may be used to program commands or operating parameters into IMD 101 for controlling the functioning of IMD 101. External device(s) 110 may be used to interrogate IMD 101 to retrieve data, including device operational data as well as physiological or neurological data accumulated in memory of IMD 101. The interrogation may be automatic, e.g., according to a schedule, or in response to a remote or local user command. One or more of these external device(s) 110 may also be referred to as an "instrument" or as a group of instruments.

Examples of communication techniques used by IMD 101 and external device(s) 110 are not limited to any particular communication technique or communication protocol, and in some examples include tissue conductance communication (TCC) or RF telemetry, which may be an RF link established via Bluetooth®, WiFi, or medical implant communication service (MICS). IMD 101 may utilize an antenna arranged as described in this disclosure, or an equivalent thereof, to perform the communications associated with IMD 101, in order to provide any of the features and to perform any of the functions ascribed to IMD 101.

In various examples, one or more of the IMDs in FIG. 1, may include the antenna arranged in accordance with the examples of antenna described in this disclosure, and any equivalents thereof, to facilitate the communications with the one or more IMDs of system 100, and/or between the one or more IMDs 101, IMD 103, IMD 105, and/or external device(s) 110. In various examples, monitoring and/or delivery of therapy by IMD 101 may be provided in conjunction with the features and functions provided by IMD 105. In some examples, IMD 105 may engage in wireless communications between IMD 105 and one or more other IMD(s) 101 and/or IMD 103 to facilitate coordinated activity between IMD 105 and these one or more other IMD(s). The wireless communication may by via TCC of radio-frequency (RF) telemetry and may be one-way communication in which one device is configured to transmit communication messages and the other device is configured to receive those messages, or two-way communication in which each device is configured to transmit and receive communication messages.

System 100 may also include an intracardiac pacing device IMD 105, in some examples. In the illustrated example, IMD 105 is implanted in the right-ventricle of patient 102, e.g., internal to the heart 104 of patient 102. In some examples, one or more IMDs (not specifically shown in FIG. 1) similar to IMD 105 may additionally or alternatively be implanted within other chambers of heart 104 or attached to the heart epicardially. IMD 105 may be configured to sense electrical activity of heart 104, and/or to deliver stimulation therapy such as pacing therapy, e.g., bradycardia pacing therapy, cardiac resynchronization therapy (CRT), anti-tachycardia pacing (ATP) therapy, and/or post-shock pacing, to heart 104. IMD 105 may be attached to an interior wall 108 of heart 104 via one or more fixation mechanisms that penetrate the tissue. As shown in FIG. 1, the fixation mechanisms may secure IMD 105 to the cardiac tissue and retain an electrode (e.g., a cathode or an anode) on the housing of IMD 105 in contact with the cardiac tissue. In addition to delivering pacing pulses, IMD 105 may be capable sensing electrical signals using the electrodes carried on the housing of IMD 105. These electrical signals may be electrical signals generated by cardiac muscle and indicative of depolarizations and repolarizations of heart 104 at various times during the cardiac cycle.

In various examples, IMD 105 is configured to wirelessly communicate with one or more external device(s) 110 as illustratively shown in FIG. 1 by communication link 112. For instance, IMD 105 may communicate with external device(s) 110 similar to the above description for IMD 101.

System 100 may include one or more additional IMDs, such as IMD 103, that may be implanted in various locations of patient 102 outside the ventricles of heart 104 of patient 102. IMD 101 is illustrative of one or more implanted devices, such as one or more implantable monitoring device, an implantable hub device, or implantable loop recorder.

IMD 103 as shown in FIG. 1, may comprise an implantable pressure sensing device that may be implanted within pulmonary artery of the patient. In some examples, the pulmonary artery may comprise a left pulmonary artery, whereas in other examples, pulmonary artery may comprise a right pulmonary artery. For the sake of clarity, a fixation assembly for IMD 103 is not depicted in FIG. 1.

As illustrated in FIG. 1, IMD 103 may be implanted, as one example, within a pulmonary artery of patient 102, and may include pressure sensing circuitry configured to measure the cardiovascular pressure within the pulmonary artery of patient 102. In some examples, IMD 103 may include wireless communication circuitry, e.g., TCC and/or RF telemetry circuitry, configured to receive a trigger signal from IMD 101 and/or IMD 105, at electrodes or an antenna provided in IMD 103 (e.g., an antenna such as one of the examples described in this disclosure). The pressure sensing circuitry of IMD 103 may be configured to measure the cardiovascular pressure of patient 102 in response to receiving the trigger signal. In either case, IMD 103 may be configured to transmit the measured pressure values to IMD 101 and/or IMD 105 by wireless communication. For example, IMD 103 may transmit measurements and data acquired by IMD 103 related to pulmonary artery pressure and other information generated by IMD 103 to IMD 101, to IMD 105, and/or to external device(s) 110. In various examples, IMD 103 comprises an antenna used for communications between IMD 103 and other devices of system 100, arranged using the examples of antennas described throughout this disclosure, or any equivalents thereof.

For the remainder of the disclosure, a general reference to a medical device system may refer collectively to include any examples of medical device system 100, as described above with respect to FIG. 1, and any equivalents thereof. Further, for the remainder of the disclosure a general reference to an IMD may refer collectively to include any examples of IMD 101, IMD 103, and/or IMD 105, as described above with respect to FIG. 1, and any equivalents thereof.

The example IMDs of FIG. 1 include a housing configured to house at least one of stimulation and sensing circuitry within an internal side of the housing. For example, a battery such as lithium/iodine cell is coupled to a motherboard that hosts one or more semiconductor chips and other electronic circuitry such as stimulation and sensing circuitry for providing stimulation to patient 104 and sensing signals (e.g., pressure, electrical, etc.) within patient 104. In some examples, the stimulation and sensing circuitry may be part of the one or more semiconductor chips.

The motherboard and the battery are encased in a housing of the IMDs. As one example, the housing may be formed with a metal cup that holds the battery and other integrated circuitry and a wafer (e.g., a non-conductive wafer made from glass, sapphire, or other material) that bonds to the metal cup. In some examples, the metal cup may be formed using titanium or a titanium alloy, as two non-limiting examples. As an example method of manufacturing, the stimulation and sensing circuitry are inserted into a metal casing, which may be in multiple pieces. The multiple pieces are hermetically sealed with the wafer to together to form a housing configured to house at least one of stimulation and sensing circuitry within an internal side (e.g., inside) of the housing.

In one or more examples described in this disclosure, an antenna having a curved (e.g., closed or partly open) structure may be coupled to an external side of the housing. For example, a thin layer of insulation (e.g., less than 1 mm such as 0.5 mm) is placed on the housing and the antenna having the curved structure is formed on the thin layer of insulation. In one example, the wafer is the thin layer of insulation. Also, the thickness of the insulation may be less than 0.5 mm, such as 0.1 mm, and may be based on the desired mechanical strength of the layer of insulation.

As one example, the antenna is deposited on the outside (e.g., on the wafer) and conductive traces are deposited on the inside surface of the wafer and the components are arranged on the inside surface as well. In one or more embodiments, the wafer can be a non-conductive or insulative substrate such that external contacts, the antenna, and any conductors or other devices disposed on the wafer can be electrically isolated if desired. The wafer can include any suitable material or combination of materials. The wafer (e.g., non-conductive wafer) can include at least one of glass, quartz, silica, sapphire, silicon carbide, diamond, synthetic diamond, and gallium nitride, or alloys or combinations (including clad structures, laminates etc.) thereof Having the antenna with the curved (e.g., closed or partially open) structure on the outside of the housing may provide various advantages. For example, after implantation, the antenna is in contact with patient tissue (e.g., directly exposed to the patient tissue). The patient tissue tends to have a relatively high dielectric constant, and the size of the antenna is inversely proportional to the dielectric constant. By placing the antenna in contact with patient tissue, the size of the antenna can be reduced substantially as compared to prior antenna architectures where the antenna is formed within a polymer having much lower dielectric constant.

As described above, in this disclosure, "in contact" may refer to an antenna being surrounded by material having a dielectric constant set by the patient tissue such that the resonant frequency of the antennas is a function of a dielectric constant of the patient tissue. In examples where the antennas are in direct contact with the skin, the resonant frequency of the antennas is a function of the dielectric constant of the skin. Stated another way, the functionality and operational characteristics of the antennas is based on a dielectric constant of the patient tissue or blood or possibly skin. As one example, the patient tissue is muscle tissue. As another example, the IMD may be surrounded by blood, and blood has a similar dielectric constant as muscle tissue. In this disclosure, although patient tissue is discussed, the example techniques may be applicable to examples where the IMD is surrounded by blood or the antenna is in contact with skin (e.g., antenna of external device 110 that placed on the skin of patient 102 to communicate with IMD 101). Accordingly, patient tissue may be considered a general term to refer to patient anatomy that surrounds the IMD such as muscle or blood or patient skin.

Figure 2:
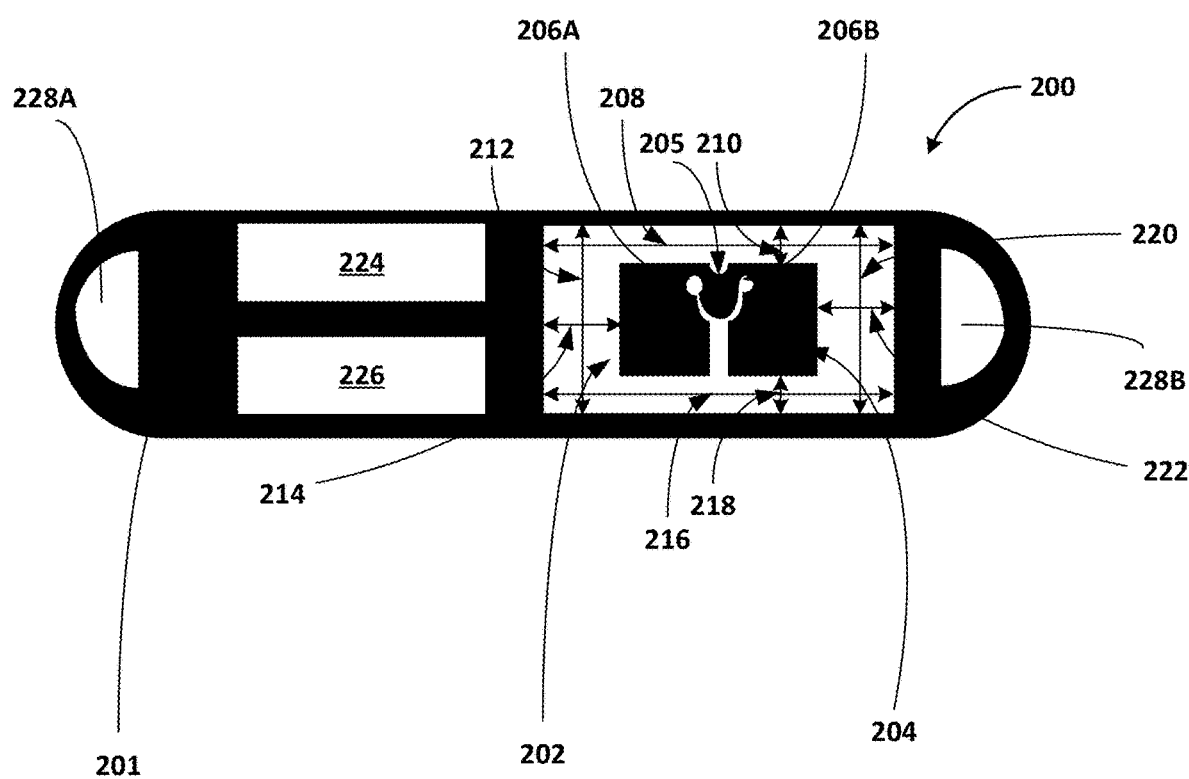
FIG. 2 is a diagram of an implantable medical device in accordance with one or more examples described in this disclosure.
Figure 3:
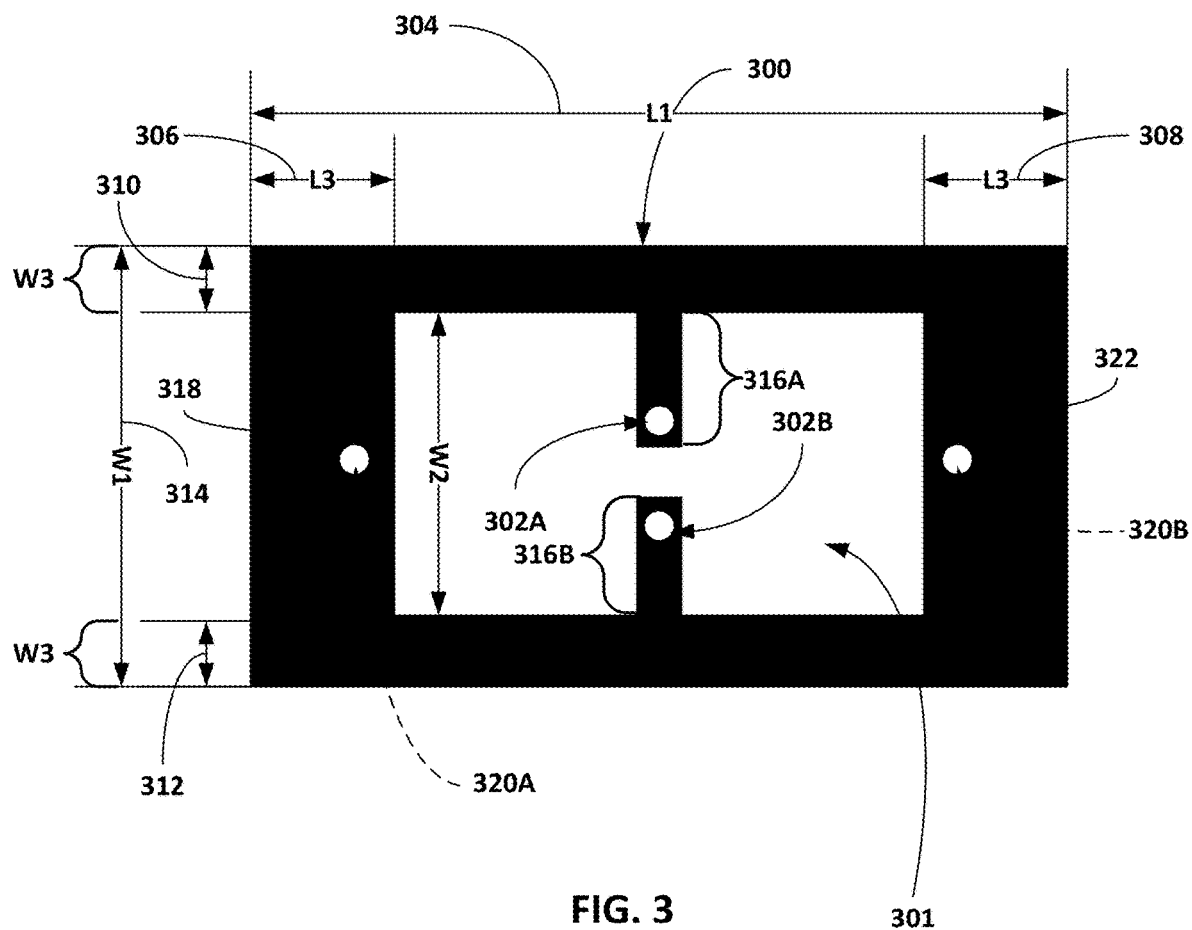
FIG. 3 is a diagram illustrating an example of an antenna in accordance with one or more examples described in this disclosure.
Figure 5:
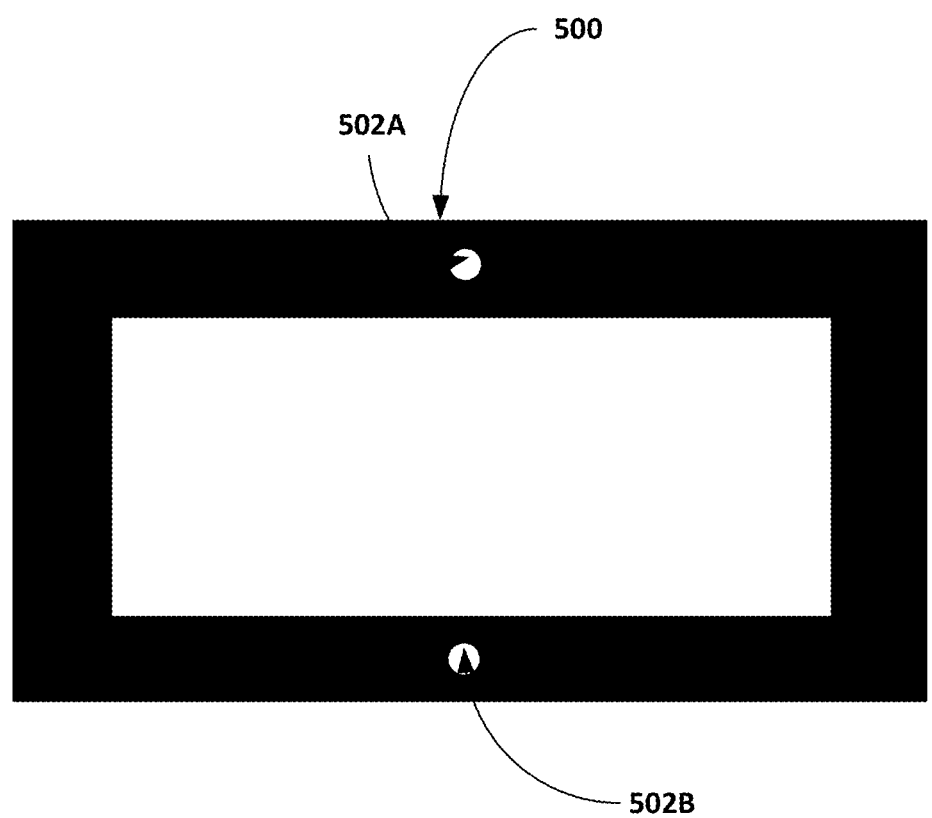
FIG. 5 is a diagram illustrating another example of an antenna in accordance with one or more examples described in this disclosure.

As one example, the equation to determine resonant frequency of example antennas described in this disclosure having the curved structure is $0.5\lambda = 0.5c_0/(f\sqrt{e_r})$, where $c_0$ is the light propagation speed in a vacuum, f is the frequency, and $e_r$ is the relative permittivity of tissue (e.g., dielectric constant). The value of $\lambda$ may be approximately one-half the width of the antenna. The example of the width is shown in FIGS. 2, 3, and 5.

The above equation to determine resonant frequency is an approximation, and numerical methods may be used to determine resonant frequency rather than an analytical equation. In other words, for a desired frequency f (e.g., 2.4 GHz), the above equation provides an approximation of the width of the curved antenna, but some level of testing and modifying may be needed to achieve the right size and shape such as based on the design of the IMD. Because the antenna is in contact with the patient tissue, in one or more examples described in this disclosure, the dielectric constant for determining the resonant frequency of the antenna is a function of the dielectric constant of the tissue surrounding the IMD.

In some examples, the dimensions of the antenna may be dependent upon the type of communication (e.g., may be frequency dependent). In the examples below that provide example dimensions of the device, may be for the BTLE communication. However, as also described below, in some examples, the example antennas may be wide range and provide good behavior over a wide range of frequencies. As noted above, the techniques to determine the dimensions of the antenna may be through a numerical method of testing different lengths and widths to achieve the desired resonant frequency for the antenna.

In some examples, the antenna may be in direct contact with the patient tissue. However, it may be possible that in some examples, a protective coating is applied to the antenna to protect the IMD. Even in such a scenario, the antenna may be considered as being "in contact" with patient tissue because the dielectric constant of the tissue is determinative of the resonant frequency of the antenna. For example, the antenna may be formed with titanium which tends to not corrode, but a coating of parylene or like substance may be used.

Antennas in prior antenna architectures may not be exposed directly to the tissue because the high conductivity of the tissue causes high losses in the radiation. For example, in prior antenna architectures, an oscillating current through the antenna causes the electromagnetic field to radiate. However, if the antenna is exposed to tissue and the housing is exposed to tissue, there is a low impedance path for the current from the antenna to the housing, which forms a ground. Therefore, rather than the current flowing through the antenna causing the electromagnetic field, a large percentage of the current flows to through the patient tissue, reducing the amplitude of the electromagnetic field that is radiated.

In these prior architectures, to avoid the antenna from being exposed to tissue, the antenna is embedded in low dielectric material body (e.g., called header). Due to the integration cost reason, often low dielectric materials such as a polymer (with dielectric constant normally 2~4) are used to insulate the antenna. Since the antenna size is inversely proportional the dielectric constant, with low dielectric constant, the antenna size is very hard to reduce, which increases the overall medical device size. Also, due to the high loss of human tissue, the insulation body is often required to be over a certain thickness, which further increases the overall medical device size. Further, to make the antenna efficient, the antenna needs to be away from the metal shield (e.g., housing is often called 'can' or 'case'), as well as other metal components in the header (such as the leads bore), which further increases the device size. Furthermore, because of the large differences in dielectric constant between the surrounding body tissue and the antenna insulation materials, the antenna impedance usually results in non-ideal number, therefore, adding a matching circuit to help the impedance match is very common in medical device design, which increases the overall complexity of the device and introduces additional power loss (i.e., reduction of device longevity).

In the examples described in this disclosure, because the antenna is on an external side of the IMD and not in a housing, the dielectric constant is based on the patient tissue which is much larger than where the antenna is embedded in polymer of a header. Therefore, the examples of the antenna described in this disclosure tend to be smaller, resulting in a smaller overall IMD. Furthermore, the antennas may be planar (e.g., with little thickness or volume), and therefore, even when coupled to an external side of the housing, do not increase the overall size of the IMD.

Because the antenna is coupled to the external side of the IMD (e.g., on the wafer), the antenna may be stacked on the wafer (e.g., the wafer such as sapphire is less than 1 mm) as compared to other prior architectures. In some examples, the wafer may be the insulation and no additional insulation is needed. In the prior architectures, if the antenna were proximate to the housing (or ground plane), the antenna would not radiate well since the current flowing in ground is in the opposite direction to the current through antenna, which results in a cancellation of radiation. The reason is that when the insulation layer dielectric constant is much lower than that of the surrounding tissue, where the antenna is in contact with, the ground cancelling effect is significantly reduced. For example, when the insulation thickness is only 0.5 mm, the antenna design in this disclosure still performs comparable to normal antenna design in polymer header. An example of the antenna stacked on an IMD is illustrated with respect to FIG. 9.

In the antenna architecture of this disclosure, the antenna is self-contained and there is no need for an additional ground for there to be a complete circuit. For example, the antenna forms a complete self-contained loop between one feed through point and ground or between the two feed through points. Accordingly, the current flows from one feed through point to the other feed point or ground rather than through the tissue. There may be some amount of current that flows from tissue between the feed through points. However, the antenna path may be of lower resistance than the tissue and therefore, there may be some loss in the amplitude of the electromagnetic wave, but the loss may be minimal.

FIG. 2 is a diagram of an implantable medical device in accordance with one or more examples described in this disclosure. For example, FIG. 2 illustrates an example of IMD 200, which is an example of IMD 101. As one example, IMD 200 has a length less than 50 millimeters (mm), a width less than 10 mm, and a height less than 5 mm. As one example, length is 45 mm, the width is 7.9 mm, and the height is 4.2 mm.

In some examples, the total volume of the IMD 200 may be less than 1500 mm$^3$, and the length, width, and height may be selectable to achieve the volume. The above dimensions are used as an example and should not be considered limiting. The example techniques described in this disclosure may be applicable to other types of medical devices.

IMD 200 includes housing 201. Housing 201 includes two parts. A first part is made from metal and forms a cup-like shape in which components of IMD 200 reside. A second part is a wafer that is bonded to the top to the top of the metal to enclose IMD 200. The wafer may be formed with at least one of glass, quartz, silica, sapphire, silicon carbide, diamond, synthetic diamond, and gallium nitride, or alloys or combinations (including clad structures, laminates etc.) thereof. In general, the wafer may be insulative (non-conductive). The metal part of housing 201 may be formed with titanium or a titanium alloy. Other example metals are possible (e.g., biocompatible metals), and if fully insulated from direct contact with tissue, then common metals, such as copper, may be possible.

Housing 201 includes in an internal side (e.g., the volume inside housing 201) and an external side (e.g., the exterior surface of the wafer that is in contact with tissue of patient 102 when IMD 200 is implanted). In the internal side, housing 201 includes circuitry such as stimulation and/or sensing circuity 224 to provide stimulation and sensing capabilities such as those described above. For example, to manufacture IMD 200, the stimulation and/or sensing circuitry 224 may be encased within pieces of housing 201 (e.g., metal portion of housing 201) and the pieces of housing 201 may be hermetically sealed (e.g., the wafer and the metal portion are hermetically sealed) to form housing 201 that includes stimulation and/or sensing circuitry 224.

Stimulation and/or sensing circuitry 224 may include, in one example, one or more sense amplifiers, filters, rectifiers, threshold detectors, comparators, analog-to-digital converters (ADCs), switches or other analog or digital components. When IMD 200 is configured to sense cardiac signals, stimulation and/or sensing circuitry 224 may include one or more sensing channels for acquiring cardiac electrical signals from two or more electrodes coupled to the stimulation and/or sensing circuitry 224. Each sensing channel may be configured to amplify, filter and rectify the cardiac electrical signal received from selected electrodes coupled to the respective sensing channel to improve the signal quality for sensing cardiac events, e.g., R-waves and P-waves.

Stimulation and/or sensing circuitry 224 may also include, in some examples, pulse generation circuitry for generating and delivering electrical stimulation therapy, such as pacing and/or defibrillation/cardioversion therapy. The pulse generation circuitry may include one or more capacitors, a charging circuit, transformer(s), switches and the like. Stimulation and/or sensing circuitry 224 may include other components for sensing non-cardiac or cardiac signals, including accelerometers, pressure sensors, biomarker sensors (such as glucose or potassium sensors), or any other type of sensor. Stimulation and/or sensing circuitry 224 may also include other types of therapy circuitry for providing therapy in addition to or instead of electrical stimulation therapy, including drug therapy, non-cardiac stimulation therapy, or any other type of therapy.

On the external side, housing 201 may include one or more electrodes 228A and 228B (as one example) for delivery of stimulation and/or for sensing. Also, in some examples, wires or other connectors may extend from housing 201 to one or more leads having electrodes for stimulation and/or sensing.

IMD 200 is configured for wireless communication with external device(s) 110 or other devices implanted within patient 102. For wireless communication, IMD 200 includes antenna 202. For example, as illustrated in FIG. 2, antenna 202 includes a feeding structure that includes feed points 205, 206A, and 206B. Feed points 206A, 206B may be coupled together (e.g., shorted together). Accordingly, feed points 206A, 206B may be considered as a single feed point 206. In some examples, rather than having feed points 206A, 206B, it may be possible to have a single feed point 206.

As one example, one of feed points 205 or 206 is coupled to communication circuitry 226 within housing 201 and the other one of feed points 205 or 206 is coupled to ground (e.g., metal of housing 201). Communication circuity 226 may include a transmitter, a receiver, or may be a transceiver. That is, communication circuitry 226 may provide for bi-directional communication (e.g., transmit and receive communication) or uni-directional communication (e.g., receive but not transmit data or transmit by not receive data). By connecting feed points 206A, 206B to ground, the example illustrated in FIG. 2 may form a ground-signal-ground because feed point 205, between feed points 206A, 206B, is coupled to communication circuitry 226. The ground-signal-ground configuration is one example. In the example where one of feed points 205 or 206 is coupled to ground, feed points 205 or 206 (e.g., 206A and 206B) is coupled to the metal portion of housing 201. As another example, feed points 205 or 206 form differential feed points, in which neither feed points 205 or 206 are coupled to ground and both feed into communication circuitry 226 within housing 201.

Feed points 205 and/or 206 may be coupled to communication circuitry 226 through housing 201, such as the wafer of housing 201. As one example, communication circuitry 226 may be coupled to a transmission line that couples to feed points 205 or 206. Communication circuitry 226 may be configured to output a current (e.g., modulated current) that flows through antenna 202 and causes antenna 202 to radiate an electromagnetic signal carrying the data that IMD 200 is to transmit. For receiving, an electromagnetic signal may cause a current on antenna 202 that communication circuitry 226 receives and demodulates to determine the data that is transmitted to IMD 200. As described above, communication circuitry 226 may be configured for uni-directional communication in some examples.

Antenna 202 may be configured to communicate in accordance one or more wireless communication protocols such as Bluetooth®, WiFi, or medical implant communication service (MICS). That is, antenna 202 may be configured to have a resonant frequency that is approximately equal to the frequency used for one or more example communication protocols. Here, approximately refers to the resonant frequency of antenna 202 being within the range of frequencies that conform to the example communication protocols.

Antenna 202 may be configured to have a curved (e.g., closed or partially open) structure. A curved structure may refer to an arbitrary antenna where the antenna forms a complete enclosed structure with connected ends with a gap separating a portion of the antenna from other portions of the antenna. Examples of a curved structure include rectangles, circles, triangles, or other fully enclosed polygons. In general, example antennas described in this disclosure may be an arbitrary curved structure. A dipole antenna or a monopole antenna are not examples of a curved structure. A pad antenna is not an example of a curved structure.

Figure 4:
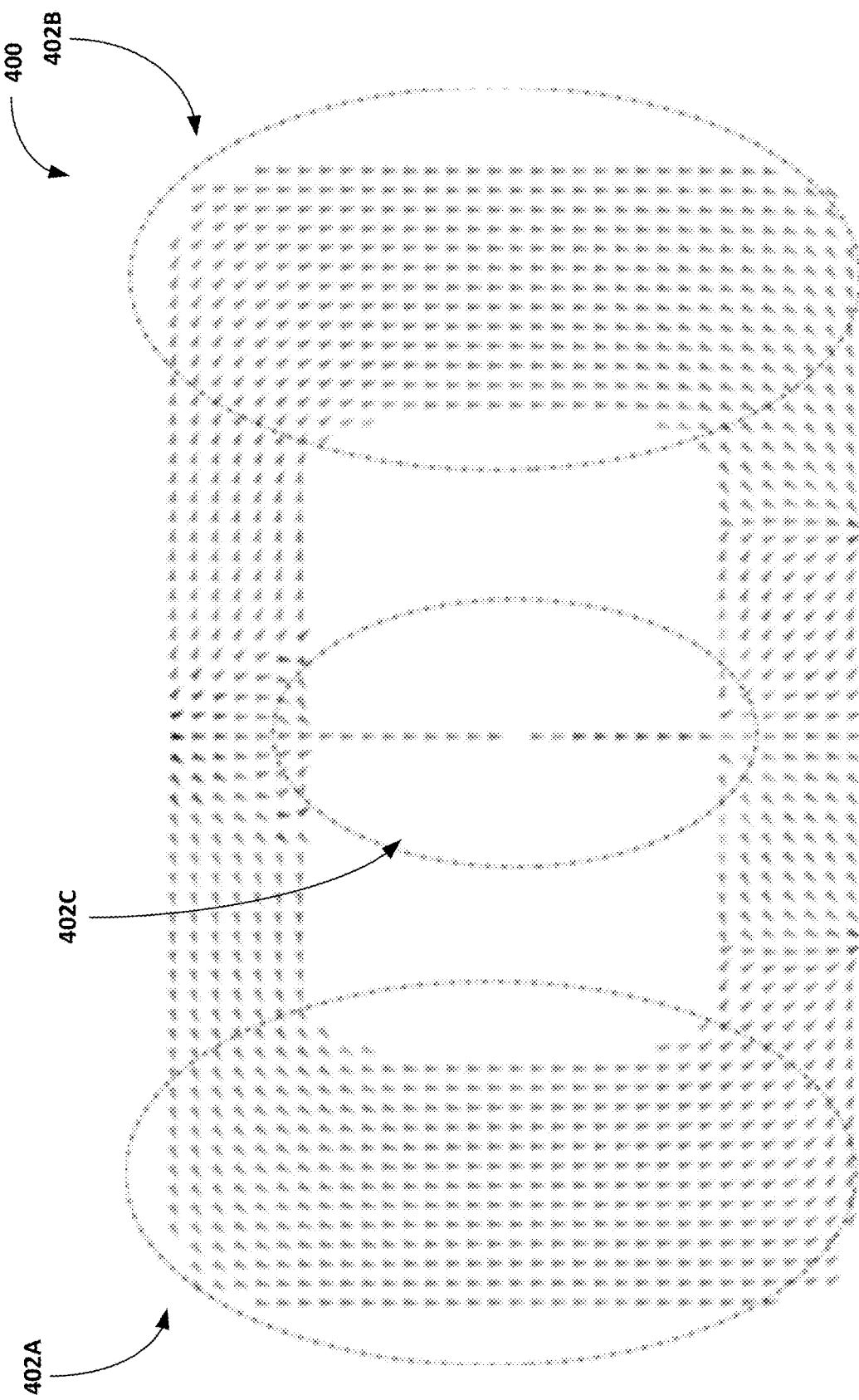
FIG. 4 is a conceptual diagram illustrating an example of current distribution on the example antenna illustrated in FIG. 3.

Although antenna 202 has a curved structure, antenna 202 may be different than conventional loop antennas. A loop antenna is formed as wires, rather than being stacked on housing 201, as illustrated in FIG. 2 and described in more detail below. Also, in a loop antenna, the current distribution is circular within the electrical wire. For instance, the current distribution in the loop antenna can be considered as going "up" one half of the loop and going "down" the other half of the loop. This type of current distribution is considered as being out-of-phase. However, in some examples, the current distribution of antenna 202 is in-phase. One example of in-phase current distribution is illustrated in FIG. 4 with respect to the example antenna 300 illustrated in FIG. 3. The in-phase current distribution of antenna 202 may be similar and not like that of a loop antenna.

In accordance with one or more examples described in this disclosure and as illustrated in FIG. 2, antenna 202 is stacked on housing 201 (e.g., stacked on the wafer portion). Antenna 202 being stacked may mean that dimensions of antenna 202 are less than the dimensions of housing 201. For example, rather than examples of loop antennas whose wires loop around the perimeter of the IMD, antenna 202 is formed on-top-of housing 201. For example, in some examples, during manufacturing, a thin layer of material (e.g., the wafer which may be less than 1 mm such as 0.5 mm and even 0.1 mm or less) is formed as part of housing 201 to enclose housing 201. The thin layer of material may be insulative material such as non-conductive material with low dielectric loss (e.g., polymer, sapphire, glass, quartz, ceramic, etc.), and antenna 202 may be formed on top of the thin layer of material.

As one example, the antenna 202 may be a planar antenna. A planar antenna may refer to antenna 202 having very little volume. For instance, the width of antenna 202 is shown by lines 208 and 216 and the length of antenna is shown by lines 212 and 220. The width of antenna 202 may be less than 7 mm (e.g., 6.4 mm) and the length of antenna 202 may be less than 18 mm (e.g., 12 mm). In one or more examples, the height of antenna 202 may be relatively small (e.g., the thickness of the metal) may be less than 50 microns. The above dimensions are provided merely as one example, and may be different based on specific implementation needs.

In some examples, the total area of antenna 202 may be less than 120 mm² (e.g., 115.2 mm²) (including the area of gap 204), and the length and width may be selectable to achieve the area. As described above, a gap may separate portions of an antenna having a curved structure. For example, in FIG. 2, there is gap 204 separating portions of antenna 202. The area of gap 204 may be less than 60 mm² (e.g., 50 mm²). Accordingly, the area of antenna 202, excluding gap 204, is more than 60 mm² (e.g., 70 mm²).

As one example, antenna 202 includes a first portion defined by a length 214 (e.g., 4 mm) and width 212 (e.g., 6.4 mm), a second portion, orthogonal to the first portion, defined by a length 208 (e.g., 18 mm) and a width 210 (e.g., 0.7 mm), a third portion, orthogonal to the second portion and parallel to the first portion, defined by a length 222 (e.g., 4 mm) and a width 220 (e.g., 6.4 mm), and a fourth portion, orthogonal to the third portion and parallel with the second portion, defined by length 216 (e.g., 18 mm) and a width 218 (e.g., 0.7 mm).

The first portion may have a length less than 5 mm and a width less than 8 mm. The second portion may have a length less than 20 mm and a width less than 1 mm. The third portion may have a length less than 5 mm and a width less than 8 mm. The fourth portion may have a length less than 20 mm and a width less than 1 mm.

As one example, length 214 and 222 may be less than 1 cm and greater than 1 mm, and in some examples less than 1 mm. Width 210 and 218 may be less than 1 cm and greater than 1 mm, and in some examples less than 1 mm. The exact sizes of length 214 and 22 and width 210 and 218 may be a matter of design choice and can be determined through a numerical method of trial-and-error. Length 208 and 216 may be based on the example equation of $0.5\lambda = 0.5c_0/(f\sqrt{e_r})$, as described above. Width 212 and 220 may be based on impedance of the tissue that is to surround antenna 202. Width 212 and 220 may also be determined based on trial and error techniques to provide the desired matching.

Gap 204 separates the first portion from the third portion and the second portion from the fourth portion. In some examples, as illustrated in FIG. 2, the portion encompassed by gap 204 may be the wafer of housing 201.

In some examples, the dimensions of the example portions may define the operational characteristics of antenna 202. For instance, the size of length 214 and 222 may define the resonant frequency of antenna 202. During manufacturing, the size of length 214 and 222 may be set so as to achieve the desired resonant frequency. An example of calculating the resonant frequency of antenna 202 may be based on numerical method of approximating the resonant frequency. The size of width 210 and 218 may define the impedance of antenna 202. For example, during manufacturing, width 210 and 218 may be controlled such that the impedance of antenna 202 is similar to the impedance of tissue that will surround antenna 202 after implantation. In this way, antenna 202 may be specifically formed to minimize reflection at the intersection (e.g., interface point) of patient tissue and antenna 202. Also, the impedance of antenna 202 may be set by width 210 and 218 so as to minimize impedance differences between the transmission lines extending from the transmit/receive circuitry (e.g., minimize reflections at feeding points 205 and 206).

As described above, antenna 202 may be a planar antenna that is stacked with housing 201. Accordingly, when IMD 200 is implanted within patient 102, antenna 202 is in contact with the tissue of patient 102. Having antenna 202 in contact with the tissue of patient 102 may be beneficial for various reasons. For example, the resonant frequency of antenna 202 is based on er, the dielectric constant, where the dielectric is the material surrounding antenna 202. Size of antenna 202 is inversely proportional to the square root of the dielectric constant. For example, to keep the resonant frequency the same, while reducing the size of antenna 202, means that material surround antenna 202 needs to have a higher dielectric constant. Therefore, having a larger dielectric constant allows for a smaller sized antenna 202 as compared to a smaller dielectric constant, and having a smaller sized antenna 202 may be beneficial to allow a smaller sized IMD 200.

The dielectric constant of patient tissue is approximately 30 to 80 for a resonant frequency of 100 MHz to several GHz. Some other examples, in which an antenna is not in contact with patient tissue (e.g., where the antenna is encased in a header that is hermetically sealed off from patient tissue), the dielectric constant tends to be approximately 2 to 4 and may be as large as 10. The dielectric constant, in examples where the antenna is in a hermetically sealed header, tends to be substantially less than the examples where antenna 204 is in contact with patient tissue. Therefore, the antennas in the hermetically sealed headers may be larger than antenna 202, which can be an undesirable characteristic of antennas.

There may be various reasons why prior architectures of antennas cannot be in contact with patient tissue and therefore are hermetically sealed. For example, in these prior architectures of antennas, rather than a current flowing through the antenna, the current may flow through patient tissue to ground, resulting in poor radiation. In the example of antenna 204, a majority of the current output from feeding points 205 and 206 (e.g., 206A, 206B) flows through antenna 204 rather than through tissue. This is because the metal of antenna 202 provides a lower impedance path as compared to tissue. In the prior architectures of antennas, the current path through the antenna to ground was a higher impedance path than the impedance path to ground via patient tissue. Accordingly, antenna 202 may not be sensitive to the conductivity of surrounding tissue.

For example, some prior architectures of antennas include dipole, monopole, or loop antennas. Dipole or monopole antenna (including anything based on dipole or monopole antennas) are mostly used for implantable devices, and their performance reduces significantly if directly contacted with tissue, because the tissue conductivity shorts the antenna to ground. Common loop antennas may be slightly better because magnetic field retains energy better in lossy tissue. However, when directly contacted with tissue, common loop antenna also suffers from poor impedance, and it is sensitive to the nearby grounding (or metal housing).

In the examples described in this disclosure, with feeding points 205 and 206 in the center, there is improvement of impedance. Also, with the in-phase current, as described below, as opposed to current flow of loop antenna, there may be less sensitivity to metal housing or ground, such as with direct contact with tissue and using a relatively low dielectric insulation layer.

As one example, antenna 202 does not require the metal of housing 201 as a ground and can therefore be considered as being "self-contained." Also, because antenna 202 may be insensitive to tissue conductivity, antenna 202 is in contact with patient tissue without degradation in operation since little to no current flows through the tissue.

In this manner, FIG. 2 illustrates an example of IMD 200 that includes housing 201 configured to house communication circuitry 226, and in some examples, at least one of stimulation and sensing circuitry 224 within an internal side of housing 201, and antenna 202, which is a planar antenna, having a curved structure, that is stacked on an external side of housing 201. In one or more examples, the resonant frequency of antenna 202 is based on a dielectric constant of tissue surrounding antenna 202 when IMD 200 is implanted. For example, antenna 202 may be in contact with tissue when IMD 200 is implanted.

Antenna 202 may also exhibit various other characteristics that are described in more detail below. For example, a current distribution of antenna 202 may be in-phase in opposite sides of antenna 202 (e.g., the current distribution in the first and third portions may be in-phase so that current is flowing in the same direction in the first and third portions). Also, the feeding structure including feeding points 206A and 206B may be located approximately in the center of antenna 202. Moreover, there may be additional feeding structures having respective feeding points that can be added to antenna 202.

FIG. 3 is a diagram illustrating an example of an antenna in accordance with one or more examples described in this disclosure. FIG. 3 illustrates antenna 300, which may be similar to antenna 202, but the feeding structure having feeding points 302A and 302B are located differently than feeding points 206A and 206B of FIG. 2. Antenna 300 may be a planar antenna having a curved structure that can be stacked on housing 201. As illustrated, feeding points 302A and 302B, which are similar to feeding points 206A and 206B, are located at the end of protrusions 316A and 316B. Feeding points 302A and 302B may be located anywhere along protrusions 316A and 316B, and in some examples, there may be no protrusions 316A and 316B, as illustrated in FIG. 5.

In some examples, rather than being only one feeding structure that includes feeding points 302A and 302B, there may be additional feeding structures, such as feeding points 320A and 320B. Feeding points 320A and 320B are identified with dashed lines to indicate that feeding points 320A and 320B are optional. Using feeding points 320A and 320B allows for polarization diversity. In some examples, feeding points 320A and 320B are orthogonal to feeding points 302A and 302B.

As illustrated, in FIG. 3, antenna 300 includes a first portion defined by length 306 and width 314, a second portion, orthogonal to the first portion, defined by length 304 and width 310, a third portion, orthogonal to the second portion and parallel to the first portion, defined by length 308 and width 314, and a fourth portion, orthogonal to the first portion and the third portion and parallel to the second portion, defined by length 304 and width 312. The dimensions of the first, second, third, and fourth portions may be same as the dimensions of the first, second, third, and fourth portions described above with respect to antenna 202. The first portion and the third portion may be considered as being on opposite sides of antenna 300, and the second portion and the fourth portion may be considered as being on opposite sides of antenna 300.

Similar to FIG. 2, there is a gap 301 between the first, second, third, and fourth portions. The dimensions of gap 301 can be determined based on the dimensions of the first, second, third, and fourth portions. For example, the length of gap 301 is approximately equal to length 304−(length 306+ length 308). The width of gap 301 is approximately equal to width 314−(width 310+width 312).

Assume that L1 equals length 304, L2 equals the length of gap 301, and L3 equals length 306 or length 308. Also, assume that W1 equals width 314, W2 equals the width of gap 301, and W3 equals width 310 or width 312. As one example, L1 equals 18 mm, L2 equals 10 mm, and L3 equals 4 mm. As one example, W1 equals 6.4 mm, W2 equals 5 mm, and W3 equals 0.7 mm.

These are example dimensions for approximately 2 to 3 GHz resonance frequency when implanted, with 2.5 GHz center frequency. L2 and W2 may determine the resonant frequency based on the dielectric constant of the tissue when implanted, L3 enhances the radiation, but can be reduced to 1 mm. Accordingly, L1=L2+2*L3, and can range from approximately 18 mm (e.g., where L2 is 10 mm and L3 is 4 mm) to 12 mm (e.g., where L2 is 10 mm and L3 is 1 mm). In some examples, L1 is less than 20 mm. W3 may also be modified. For example, W3 may be a minimum of 0.5 mm. Accordingly, W1 (e.g., width 314) may be approximately 6.4 mm (e.g., where W2 is 5 mm and W3 is 0.7 mm) to 6 mm (e.g., where W2 is 5 mm and W3 is 0.5 mm).

FIG. 3 also illustrates a current distribution through antenna 300. The current distribution is shown in more detail in FIG. 4. For ease, in FIG. 3, current distribution through the first portion is shown with arrow 318 and current distribution through the third portion is shown with arrow 322. As can be seen, the direction of arrow 318 and arrow 322 is the same (e.g., pointing downwards), which means that the current distribution through the first portion and the current distribution through the third portion is in the same direction. When the current distribution through the first portion and the current distribution through the third portion are in the same direction, the current distributions can be considered as being in-phase.

The current distribution of antenna 300 may be different than that of a loop antenna. In a loop antenna, the direction of the current distribution through one portion of the loop antenna would be opposite to the direction of the current distribution through an opposite portion of the loop antenna. For instance, the current can be considered as looping through the antenna such that if the current is going up in one portion it would be going down in the opposite portion (analogizing to a Ferris wheel, at the top, the bucket will start to move down, and at the bottom (e.g., opposite to the top), the bucket will start to move up).

Accordingly, antenna 300 is an example of an antenna having a curved structure formed on an external side of the housing (e.g., housing 201). Antenna 202 may be similar to antenna 300. Also, a current distribution of antenna 300 is in-phase in opposite sides of antenna 300.

FIG. 4 is a conceptual diagram illustrating an example of current distribution on the example antenna illustrated in FIG. 2 or 3. At the resonant frequency, the current distribution is as shown in FIG. 4, where the antenna (e.g., antenna 300 used for illustration purposes) is located inside the human tissue. For example, current distribution 400 is the current distribution of antenna 202 or antenna 300.

As illustrated, most of the current are in sides 402A and 402B and the center line 402C. Sides 402A and 402B correspond to the first portion and the third portion of antenna 300. Center line 402C corresponds to protrusions 316A and 316B. In the example illustrated in FIG. 4, the current distribution through sides 402A, 402B, and 402C are all in the same direction (e.g., in-phase). The in-phase current distribution may result in an enhanced radiation on the direction perpendicular to the antenna plane to outside the human body.

FIG. 5 is a diagram illustrating another example of an antenna in accordance with one or more examples described in this disclosure. FIG. 5 illustrates antenna 500, which may be similar to antenna 300 but does not include protrusions 316A and 316B. The dimensions of antenna 500 may be similar to those of antenna 300 or antenna 202.

Figure 6:
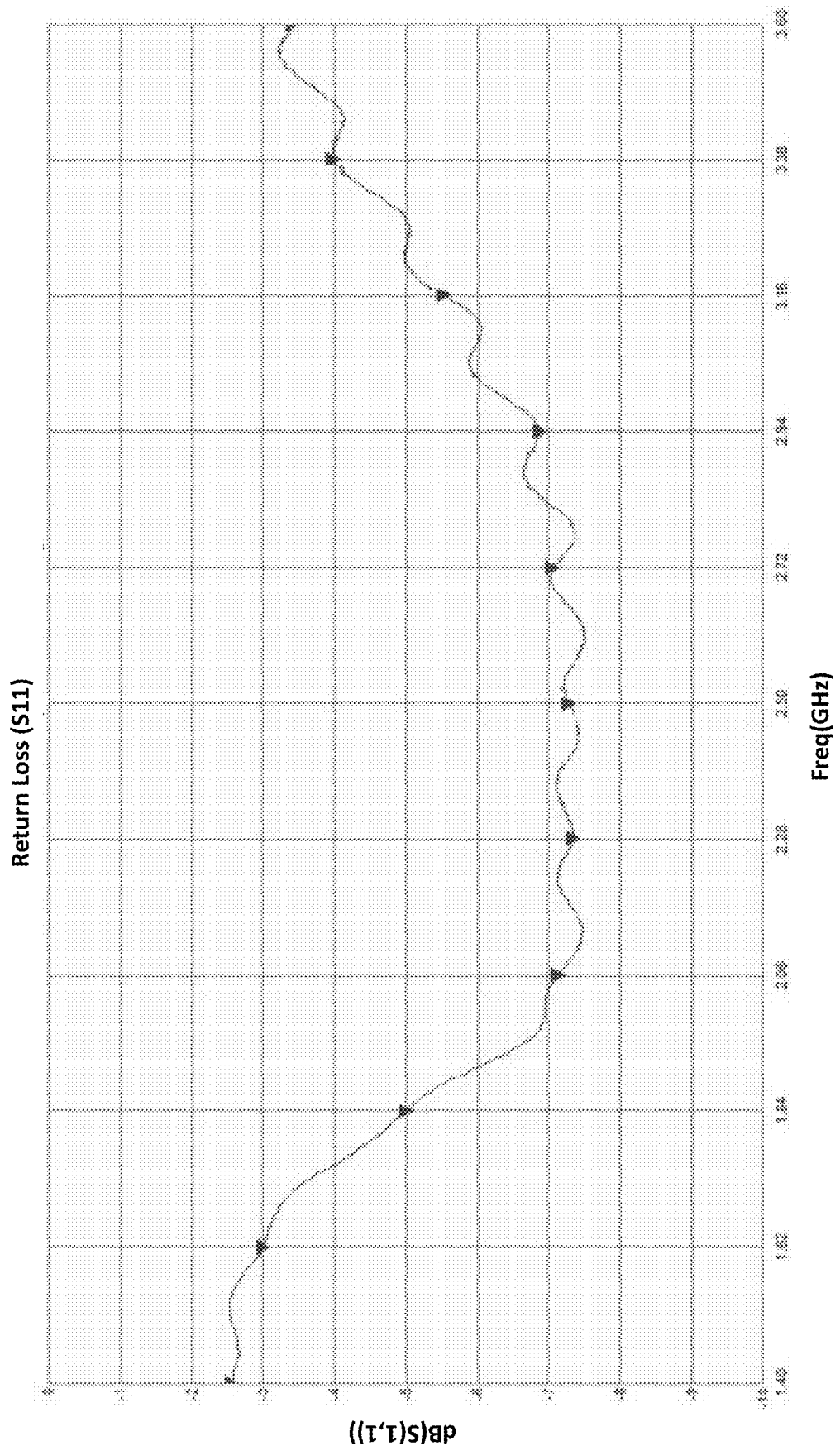
FIG. 6 is a graph illustrating an example of return loss of an antenna in accordance with one or more examples described in this disclosure.

FIG. 6 is a graph illustrating an example of return loss of an antenna in accordance with one or more examples described in this disclosure. In general, FIG. 6 illustrates the example performance of antennas like antennas 202, 300, or 500. The example of FIG. 6 is generated by placing an example antenna in simulated tissue (e.g., artificial tissue having similar characteristics of human tissue) and determining its electrical characteristics, like S11. S11 represents how much power is reflected from the antenna, which indicates how much power was not radiated.

For example, FIG. 6 illustrates the amount of power that is reflected by the antenna as a function of frequency. As illustrated, near the frequencies of interest (e.g., 2.4 GHz for Bluetooth®), the S11 is approximately −7.3 dB, which means that less than 20% of the power is reflected back, even without the use of a matching circuit, which is sometimes used to match impedances. Such performance may be much better than normal antenna designs (monopole, dipole, or loop).

Moreover, FIG. 6 illustrates that the antenna has a relatively wide band of operation. For example, the S11 is less than 6 dB between 2 to 3 GHz, which means that the example antennas described in this disclosure may be useable for wide range of frequencies, where the amount of power that is radiated is approximately 80% or greater.

Also, the example of FIG. 6 is tested using an example curved antenna that is stacked on the non-conductive wafer, with the wafer having a thickness of less than 1 mm, for instance 05. mm. In other words, the S11 was measured in a condition where the antenna is less than 1 mm above ground. Only 1 mm separating antenna from ground usually results in very narrow bandwidth. However, the example antennas described in this disclosure show good S11 (e.g., return loss) over a wide frequency range.

Figure 7:
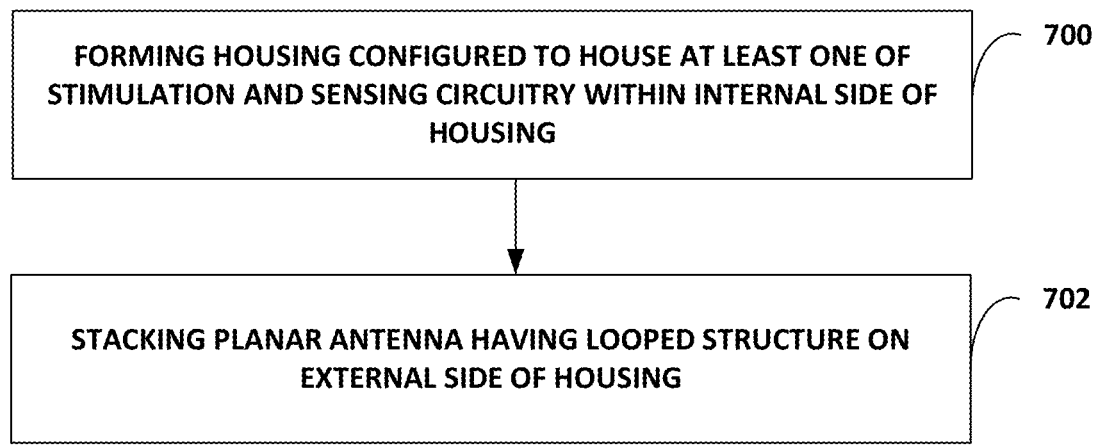
FIG. 7 is a flowchart illustrating an example method of manufacturing in accordance with one or more examples described in this disclosure.

FIG. 7 is a flowchart illustrating an example method of manufacturing in accordance with one or more examples described in this disclosure. Part of manufacturing an IMD (e.g., IMD 200) may be forming housing 201 where housing 201 is configured to house at least one of stimulation and sensing circuitry (e.g., stimulation and/or sensing circuitry 224) within an internal side of housing 201 (700). For example, housing 201 may be formed from a plurality of pieces and the stimulation and sensing circuitry 224 may be encased by the pieces, and then housing 201 is hermetically sealed.

Part of manufacturing IMD 200 includes stacking a planar antenna (e.g., antenna 202, 300, or 500), having a curved (e.g., closed or partly open) structure on an external side of housing 201 (702). For example, the manufacturing may be include forming a non-conductive wafer (e.g., with thickness less than 1 mm) that is bonded with a metallic cup, where the non-conductive wafer forms the side of the housing 201. Antenna 202, 300, or 500 is bonded to the external side of the non-conductive wafer (e.g., the portion that will be in contact with tissue).

In some examples, the manufacturing of IMD 200 may include forming a first feeding structure with feeding points (e.g., 205, 206, 302A, 302B, 502A, or 502B) and in some examples, forming a second feeding structure with orthogonal feeding points (e.g., feeding points 320A and 320B). Forming the feeding structure(s) may include creating a connection through housing 201 to transmission lines that couple the feeding points to stimulation and sensing circuitry 224 of IMD 200.

Figure 8:
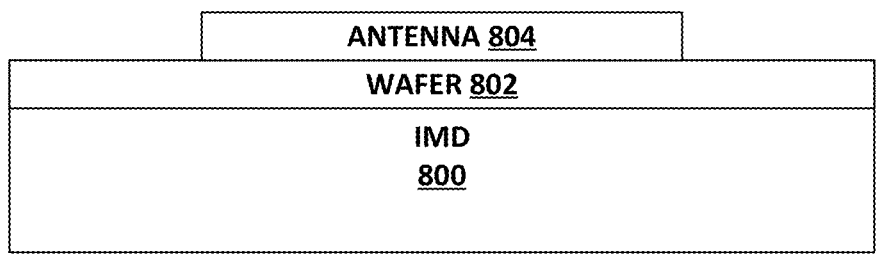
FIG. 8 is a block diagram illustrating an example of stacked architecture of an antenna on an implantable medical device.

FIG. 8 is a block diagram illustrating an example of stacked architecture of an antenna on an implantable medical device. As illustrated in FIG. 8, wafer 802 is formed part of the housing of IMD 800. For instance, wafer 802 may be bonded to the metal cup and wafer 802 and the metal cup together form the housing the houses components of IMD 800.

IMD 800 may be any of the IMDs described above. In some examples, the thickness of wafer 802 may be less than 1 mm (e.g., 0.5 mm or 0.1 mm or less than 0.1 mm). Wafer 802 may be non-conductive material with low dielectric loss such as polymer, sapphire, glass, quartz, ceramic, and the like. Antenna 804 is formed on top of wafer 802. When implanted antenna 804 is exposed to tissue 806 (e.g., muscle or blood). Antenna 804 may be any of the antennas described above.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. An implantable medical device (IMD) comprising:
a housing configured to house communication circuitry within an internal side of the housing; and
a planar antenna, having a curved structure, that is stacked on an external side of the housing and coupled to the communication circuitry, wherein the planar antenna having the curved structure forms an enclosed structure with connected ends with a gap separating a portion of the planar antenna from other portions of the planar antenna.

2. The IMD of claim 1, wherein a resonant frequency of the planar antenna is based on a dielectric constant of tissue surrounding the planar antenna when the IMD is implanted.

3. The IMD of claim 1, wherein the planar antenna is configured such that a current distribution of the planar antenna is in-phase in opposite sides of the antenna.

4. The IMD of claim 1, wherein the IMD is configured such that the planar antenna is in contact with tissue when the IMD is implanted.

5. The IMD of claim 1, wherein the planar antenna comprises a feeding structure located at approximately a center of the planar antenna.

6. The IMD of claim 5, wherein the feeding structure comprises a first feeding structure, the planar antenna further comprising a second feeding structure.

7. The IMD of claim 1, wherein the planar antenna comprises a width less than or equal to approximately 7 millimeters (mm) and a length less than or equal to approximately 18 mm.

8. The IMD of claim 1, wherein the housing comprises a width of less than or equal to approximately 10 mm, a length less than or equal to approximately 45 mm, and a height less than or equal to approximately 5 mm.

9. The IMD of claim 1, wherein the housing comprises a non-conductive wafer, wherein the planar antenna is stacked on the non-conductive wafer, and wherein the planar antenna is not within a header formed on or coupled to the housing.

10. The IMD of claim 1, wherein the planar antenna comprises a first portion having a length less than or equal to approximately 5 mm and width less than or equal to approximately 8 mm, a second portion that is orthogonal to the first portion having a length less than or equal to approximately 20 mm and width less than or equal to approximately 1 mm, a third portion that is parallel with the first portion and orthogonal with the second portion having a length less than or equal to approximately 5 mm and width less than or equal to approximately 8 mm, and a fourth portion that is parallel to the second portion and orthogonal to the first and third portions having a length less than or equal to approximately 20 mm and width less than or equal to approximately 1 mm.

11. The IMD of claim 1, further comprising at least one stimulation and sensing circuitry to provide electrical stimulation or sense electrical signals through one or more electrodes coupled to the IMD.

12. A method of manufacturing an implantable medical device (IMD), the method comprising:
forming a housing configured to house communication circuitry within an internal side of the housing;
stacking a planar antenna, having a curved structure, on an external side of the housing, wherein the planar antenna having the curved structure forms an enclosed structure with connected ends with a gap separating a portion of the planar antenna from other portions of the planar antenna; and
coupling the planar antenna with the communication circuitry.

13. The method of claim 12, further comprising forming a feeding structure located at approximately a center of the planar antenna.

14. The method of claim 12, wherein the feeding structure comprises a first feeding structure, the method further comprising forming a second feeding structure.

15. The method of claim 12, wherein the housing comprises a non-conductive wafer, wherein stacking the planar antenna comprises stacking the planar antenna on the non-conductive wafer that forms part of the housing, and wherein the planar antenna is not within a header formed on or coupled to the housing.

16. An implantable medical device (IMD) comprising:
a housing configured to house communication circuitry within an internal side of the housing; and
an antenna having a curved structure formed on an external side of the housing and coupled to the communication circuitry, wherein a resonant frequency of the antenna is based on a dielectric constant of tissue surrounding the antenna when the IMD is implanted, and wherein a current distribution of the antenna is in-phase in opposite sides of the antenna, wherein the planar antenna having the curved structure forms an enclosed structure with connected ends with a gap separating a portion of the planar antenna from other portions of the planar antenna.

17. The IMD of claim 16, wherein the antenna is a planar antenna that is stacked on the external side of the housing.

18. The IMD of claim 16, wherein the IMD is configured such that the antenna is in contact with tissue when the IMD is implanted.

19. The IMD of claim 16, wherein the antenna comprises a feeding structure located at approximately a center of the antenna.

20. The IMD of claim 19, wherein the feeding structure comprises a first feeding structure, the planar antenna further comprising a second feeding structure.

21. The IMD of claim 16, wherein the planar antenna comprises a width less than or equal to approximately 7 millimeters (mm) and a length less than or equal to approximately 18 mm.

22. The IMD of claim 16, wherein the housing comprises a width of less than or equal to approximately 10 mm, a length less than or equal to approximately 45 mm, and a height less than or equal to approximately 5 mm.

23. The IMD of claim 16, further comprising at least one stimulation and sensing circuitry to provide electrical stimulation or sense electrical signals through one or more electrodes coupled to the IMD.

24. The IMD of claim 16, wherein the housing comprises a non-conductive wafer, wherein the planar antenna is stacked on the non-conductive wafer, and wherein the planar antenna is not within a header formed on or coupled to the housing.

* * * * *